(12) United States Patent
Narula et al.

(10) Patent No.: US 6,289,547 B1
(45) Date of Patent: Sep. 18, 2001

(54) SURGICAL SCRUB DEVICE

(76) Inventors: Vinod Narula, 1168 Whetstone Way, Louisville, KY (US) 40223; Dipak Narula, 910 Cherokee Rd., Louisville, KY (US) 40204

( * ) Notice: Subject to any disclaimer, the term of this patent is extended or adjusted under 35 U.S.C. 154(b) by 0 days.

(21) Appl. No.: 09/460,054

(22) Filed: Dec. 13, 1999

Related U.S. Application Data

(60) Provisional application No. 60/159,721, filed on Oct. 15, 1999, and provisional application No. 60/151,643, filed on Aug. 31, 1999.

(51) Int. Cl.[7] .................................................. A45D 29/17
(52) U.S. Cl. ........................ 15/167.3; 15/106; 15/114; 15/104.94
(58) Field of Search ......................... 15/106, 110, 113, 15/114, 104.94, 167.2, 167.3, 187, 244.3, 244.4

(56) References Cited

U.S. PATENT DOCUMENTS

| | | | |
|---|---|---|---|
| D. 236,564 | * 9/1975 | Kaufman | 15/114 |
| D. 242,668 | 12/1976 | Kaufman . | |
| D. 287,430 | 12/1986 | Kaufman . | |
| 1,856,289 | 5/1932 | Owens . | |
| 2,186,832 | 1/1940 | Hertzberg . | |
| 2,584,515 | 2/1952 | Udell . | |
| 2,845,644 | 9/1958 | Wisner . | |
| 2,946,074 | * 7/1960 | Caldwell | 15/114 |
| 3,181,193 | 5/1965 | Nobles et al. . | |
| 3,354,492 | * 11/1967 | Baumgartner | 15/106 |
| 3,467,978 | * 9/1969 | Golden | 15/114 |
| 3,611,468 | * 10/1971 | Michael | 15/104.93 |
| 3,641,610 | 2/1972 | Lewis, Jr. . | |
| 3,694,845 | 10/1972 | Engelsher . | |
| 3,707,012 | 12/1972 | Lane . | |
| 3,966,335 | * 6/1976 | Abramson | 15/114 |
| 4,152,804 | * 5/1979 | Morris | 15/104.94 |
| 4,181,446 | 1/1980 | Kaufman . | |
| 4,203,857 | 5/1980 | Dugan . | |
| 4,283,808 | * 8/1981 | Beebe | 15/167.1 |
| 4,420,853 | * 12/1983 | Gilman et al. | 15/106 |
| 4,480,351 | 11/1984 | Koffler . | |
| 4,691,403 | 9/1987 | Scharf . | |
| 4,730,949 | 3/1988 | Wilson . | |
| 4,859,102 | 8/1989 | Chamieh . | |
| 4,866,806 | 9/1989 | Bedford . | |
| 4,880,111 | 11/1989 | Bagwell et al. . | |
| 4,903,365 | 2/1990 | Kaufman . | |
| 4,969,226 | 11/1990 | Seville . | |
| 5,035,468 | 7/1991 | Brown et al. . | |
| 5,090,832 | 2/1992 | Rivera et al. . | |
| 5,302,385 | 4/1994 | Khan et al. . | |
| 5,302,392 | 4/1994 | Karakelle et al. . | |
| 5,305,489 | * 4/1994 | Lage | 15/207.2 |
| 5,312,197 | 5/1994 | Abramson . | |
| 5,479,673 | 1/1996 | Carton . | |
| 5,596,785 | 1/1997 | Park . | |
| 5,673,454 | * 10/1997 | Quintanilla et al. | 15/167.2 |
| 6,042,287 | * 3/2000 | Kaufman | 15/114 |

FOREIGN PATENT DOCUMENTS 0206089   12/1986   (EP) .

* cited by examiner

*Primary Examiner*—Terrence R. Till
(74) *Attorney, Agent, or Firm*—Joan L. Simunic; Middleton Reutlinger

(57) ABSTRACT

The present invention is a surgical scrub device that includes a semi-rigid body, at least one row of bristles projecting from the body, and a sponge attached to the body. The design and dimensions of the scrub device are such that the user can wash the palms and the backs of the hand, and under the fingernails and between the fingers, without the need to exchange a sponge for a brush. Optionally, the scrub device can further a cleansing agent impregnated within the sponge, or housed in a reservoir within the body.

29 Claims, 10 Drawing Sheets

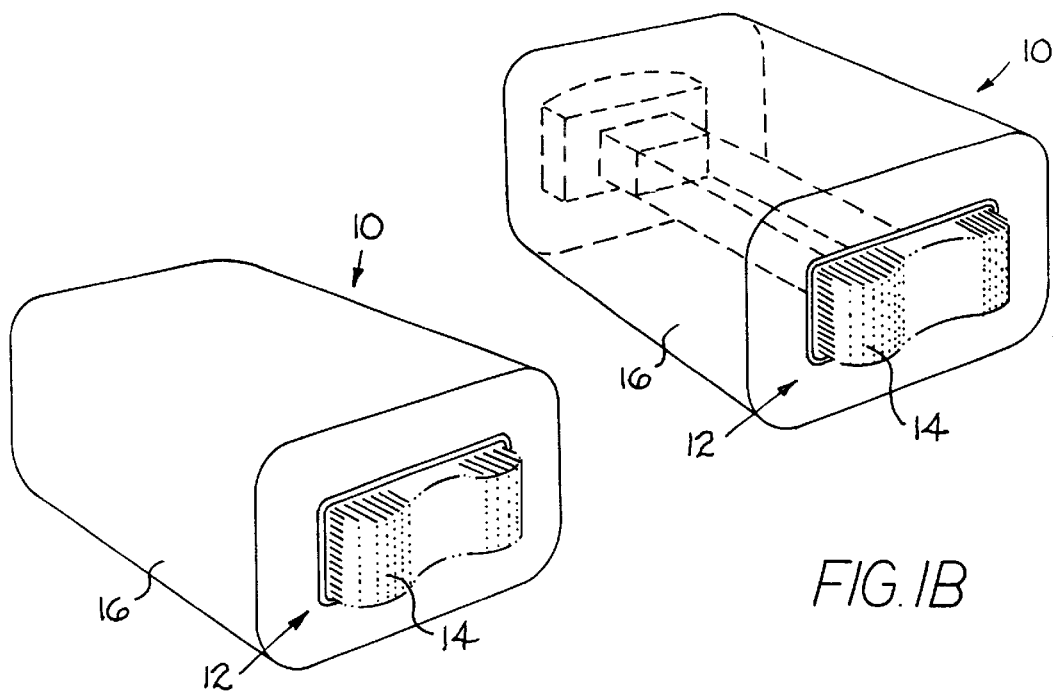
FIG. 1A
FIG. 1B
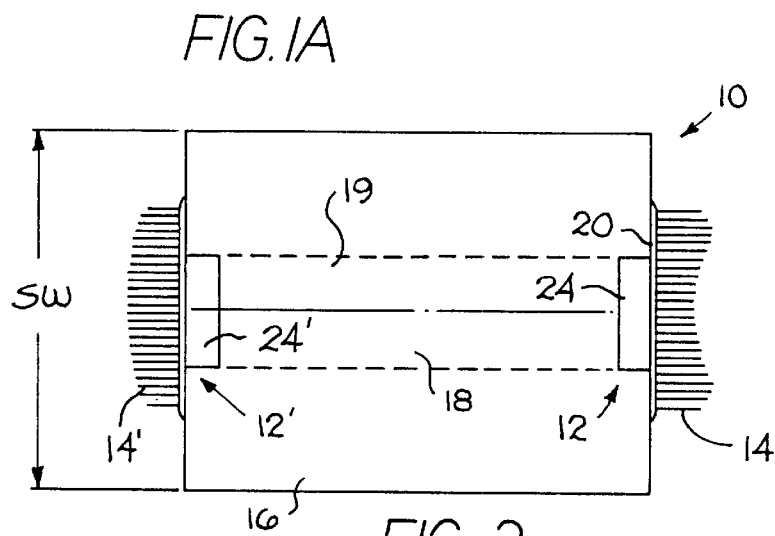
FIG. 2
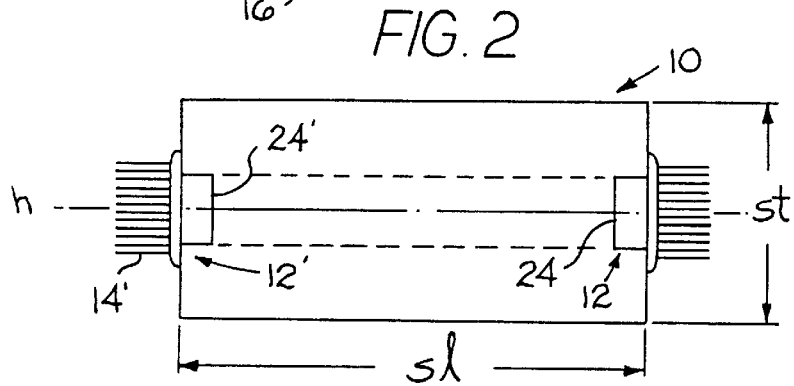
FIG. 3

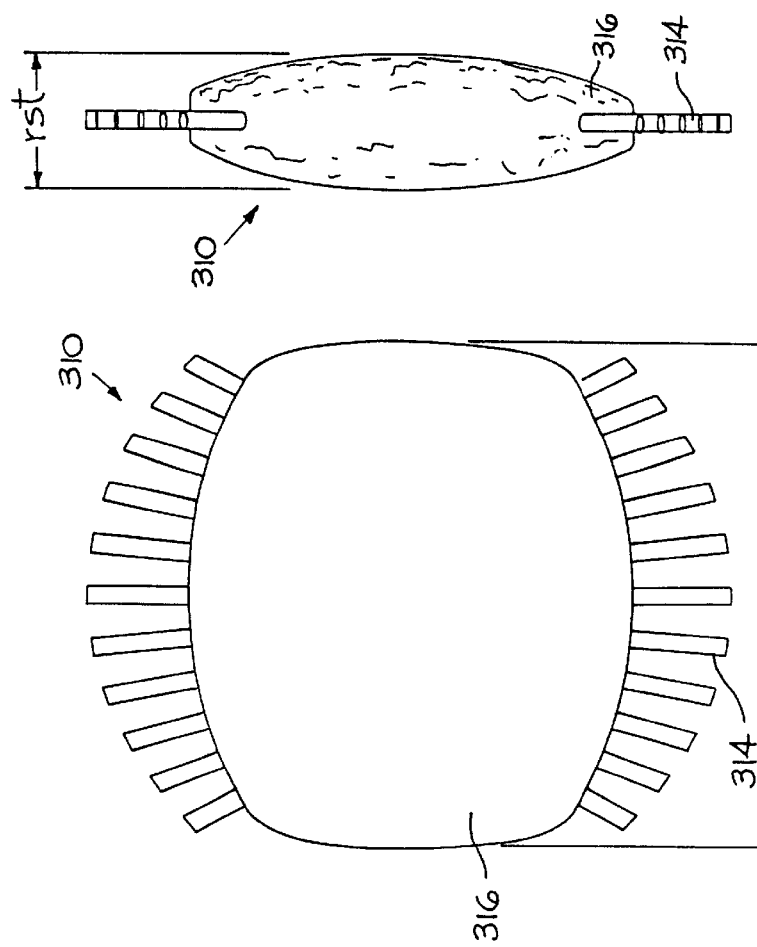
FIG. 14
FIG. 13
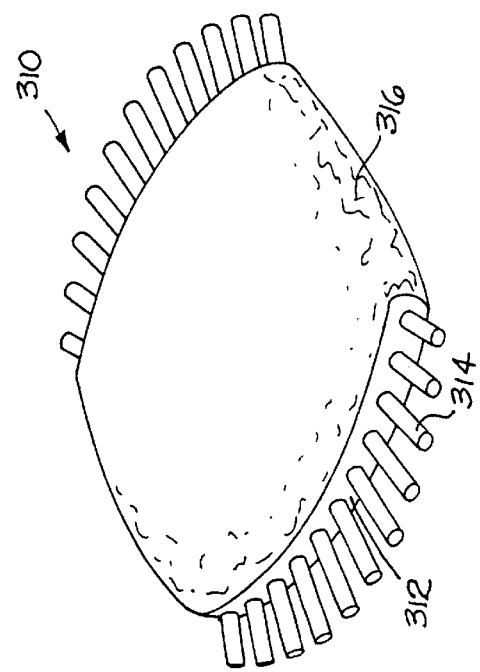
FIG. 12

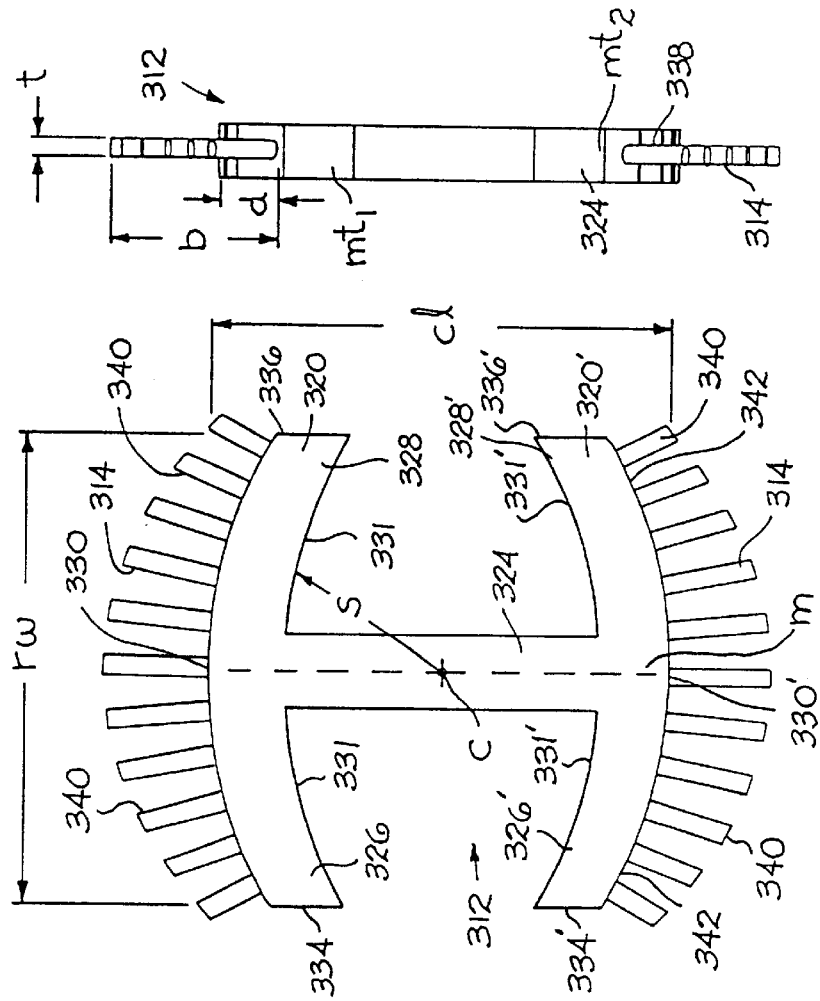
FIG. 17
FIG. 16
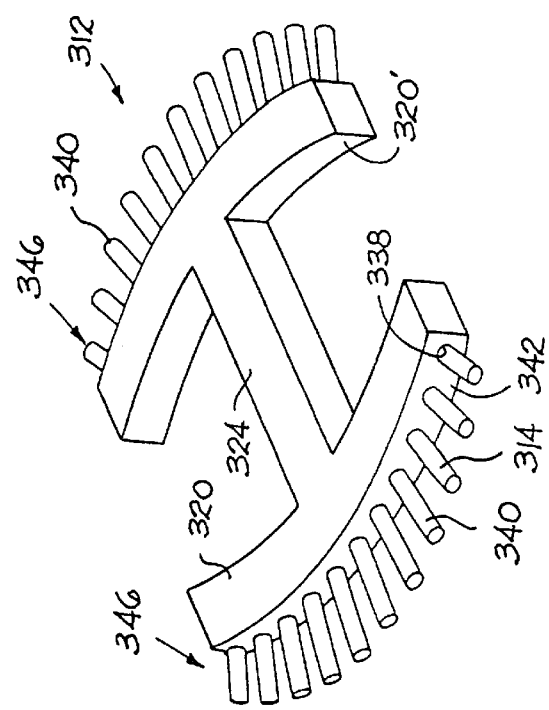
FIG. 15

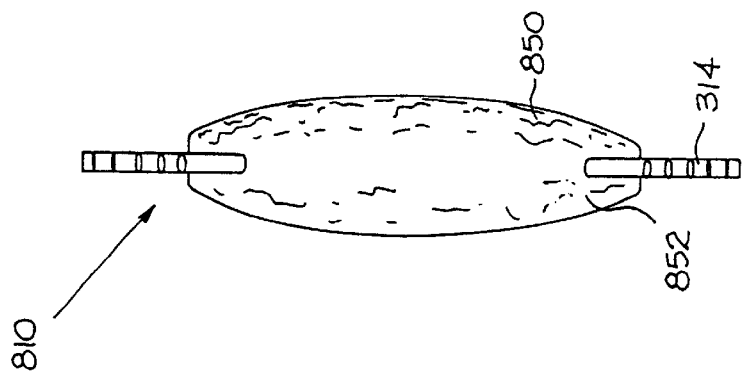
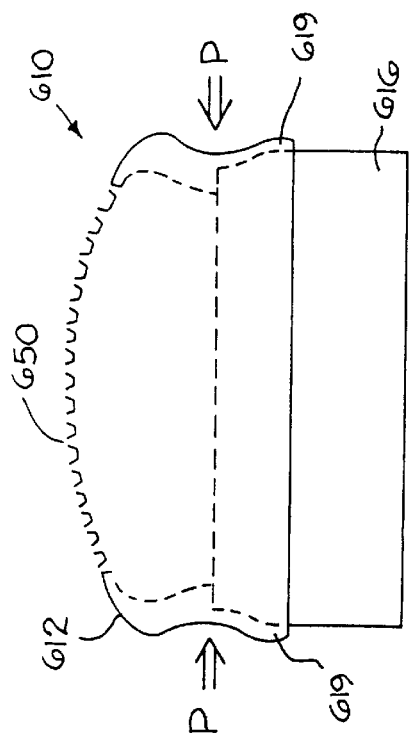
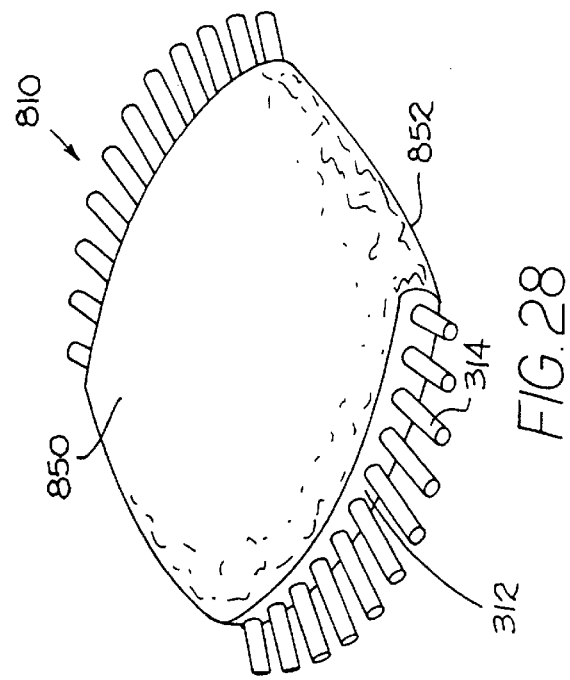

SURGICAL SCRUB DEVICE

CROSS-REFERENCE TO RELATED APPLICATIONS

This application claims priority from U.S. Provisional Application Ser. No. 60/159,721, filed Oct. 15, 1999, and to U.S. Provisional Application Ser. No. 60/151,643, filed Aug. 31, 1999, which applications are incorporated herein by reference in their entirety.

BACKGROUND

The present invention relates to a scrub device for scrubbing hands in preparation for surgical or medical procedures.

It is known that surgeons and other members of the surgical team must scrub their hands with disinfectant to reduce the risk of contamination in the operating room. Sponges are commonly used to clean the palms, the backs of the hands, and the arms. Because the areas under the nails, along the cuticles, and between the fingers can harbor bacteria, special care must be taken to diligently scrub these sites. To reach these areas, the sponges may be sculpted to include toothed regions, such as described in U.S. Pat. No. 4,866,806, or the cleaning device may replace the sponge on one face with bristles, such as described in U.S. Pat. Nos. 4,730,949 and 4,181,446. However, these toothed sponges and bristled cleaning devices typically do not fit comfortably between the fingers to scrub all the crevices on the hand. Thus, it would be advantageous to have a scrub sponge with bristles for cleaning the arm and hand, including under the nails and into the crevices on the hand, that is easy to hold and manipulate. Preferably, because it can be difficult for the surgeon to manipulate cleansing product bottles while scrubbing, the sponge would also include the cleansing product, either impregnated in the sponge or held in a reservoir within the sponge, as is known in the art.

SUMMARY OF THE INVENTION

The present invention is a surgical scrub device that includes a semi-rigid body, at least one row of bristles projecting from the body, and a sponge attached to the body. The scrub device allows the user to wash the palms and the backs of the hand, and under the fingernails and between the fingers, without the need to exchange a sponge for a brush.

In a preferred embodiment, the scrub device further includes a sponge with a disinfecting soap or with antibacterial agents impregnated within the sponge. In another preferred embodiment, the scrub device further includes a reservoir that can contain a disinfecting soap or antibacterial agent in a liquid, gel, or powder form. The soap is released from the reservoir by applying pressure to the device.

DESCRIPTION OF FIGURES

FIGS. 1a and 1b are perspective views of a surgical scrub device made in accordance with the present invention;

FIG. 2 is a top view of the device of FIG. 1a;

FIG. 3 is a side view of the device of FIG. 1a;

FIG. 4 is a top view of a body of the device of FIG. 1a;

FIG. 5 is a side view of a body of the device of FIG. 1a;

FIGS. 6a–6c are perspective views of various bristle configurations for the device of FIG. 1a;

FIG. 7 is a perspective view of the sponge of the device of FIG. 1a;

FIG. 12 is a perspective view of an alternative embodiment of the device of FIG. 10 wherein the body configuration is varied, the bristles are bundled natural fibers, and a one-piece foam sponge surrounds the body;

FIG. 13 is a front view of the device of FIG. 12;

FIG. 14 is a side view of the device of FIG. 12;

FIG. 15 is a perspective view of the device of FIG. 12, with the sponge removed;

FIG. 16 is a front view of the device of FIG. 12, with the sponge removed;

FIG. 17 is a side view of the device of FIG. 12, with the sponge removed;

FIG. 24 is a side view of the device of FIG. 21 showing an alternative pore structure in the open position;

FIG. 28 is a perspective view of an alternative embodiment of the device of FIG. 12 wherein the sponge is replaced by netting; and FIG. 29 is a side view of the device of FIG. 28.

DETAILED DESCRIPTION OF THE PREFERRED EMBODIMENT

Figure 4:
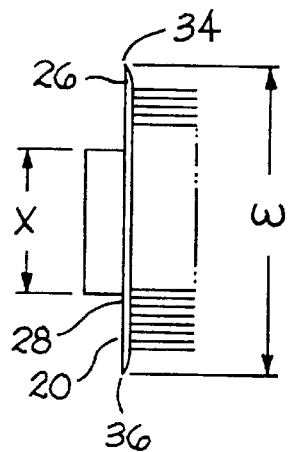
Figure 5:
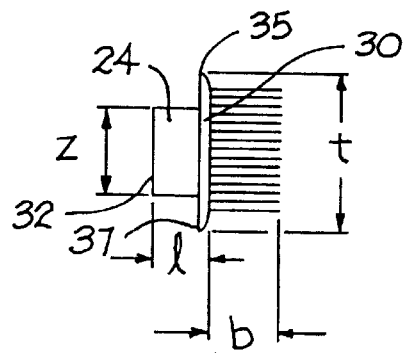

The surgical scrub devices in the various Figures are selected solely for the purposes of illustrating the invention. Other and different scrub devices may utilize the inventive features described herein as well.

Reference is first made to FIGS. 1–7 in which the device constructed in accordance with the present invention is generally noted by the character numeral 10. The device 10 has as major components at least one semi-rigid body 12, bristles 14, and a sponge 16. The body 12 has a head 20 and a trunk 24, and the bristles 14 project from the head 20. The sponge 16 surrounds the trunk 24, leaving the bristles 14 exposed. The overall dimensions of the device 10 are such that the user can easily hold the device 10 in one hand, and wash the skin and brush under the nails of other hand.

Referring again to FIGS. 4–6c, the body 12 is made from any plastic or polymer that can be molded into a semi-rigid part, such as polyethylene, polypropylene, polystyrene, thermoplastic polyester, polycarbonate, polyurethane, high density linear polyethylene, polyvinyl chloride (PVC), polyethylene terephthalate (PET), amorphous polyethylene terephthalate (APET), high density polyethylene/ethylvinyl acetate (HDPE/EVA) copolymer, glycol-modified polyethylene terephthalate (PETG), acrylonitrile butadiene styrene (ABS), cellulose acetate, or combinations thereof. The body 12 has a head 20 attached to a trunk 24, which bisects the head 20 forming left 26 and right 28 branches. The body 12 has a length "l", defined as the distance from the outside edge 30 of the head 20 to the tail end 32 of the trunk 24; a head width "w", defined as the distance from the outermost edge 34 of the right arm 26 to the outermost edge 36 of the left arm 28; a head thickness "t", defined as the distance from the upper edge 35 to the lower edge 37 of the head 20; a trunk width "x"; and a trunk thickness "z". The trunk 24 defines a horizontal plane "h".

Figure 6A:
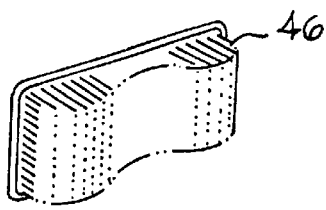
Figure 6B:
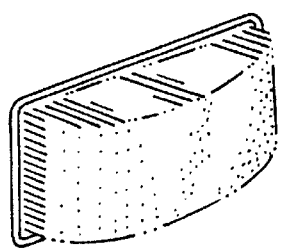
Figure 6C:
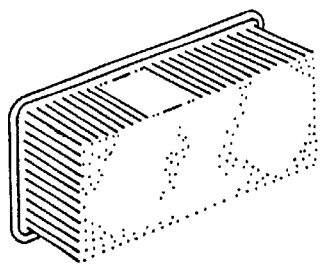

The bristles 14 are made from any plastic or polymer that can be co-extruded with the body 12, and are preferably co-extruded so as to protrude a distance "b" from the outside edge 30 of the head 20 forming a brush-like structure 46. (The term "co-extruded" refers to a manufacturing process wherein the polymer for the bristles is extuded toward the mold forming the body as the polymer for the body is fed into the mold.) Because the bristles 14 are co-extruded with the body 12, they 14 line in the same horizontal plane or in essentially parallel horizontal planes to the trunk 24. Depending on the application, the bristles 14 may span the head 20 in a single continuous row (not shown), in a series of rows (FIGS. 6a–6c), or in a random pattern (not shown). The distance "b" may be essentially equal for each bristle, as shown in FIG. 6c, or may vary, such as shown in FIGS. 6a, 6b.

Figure 7:
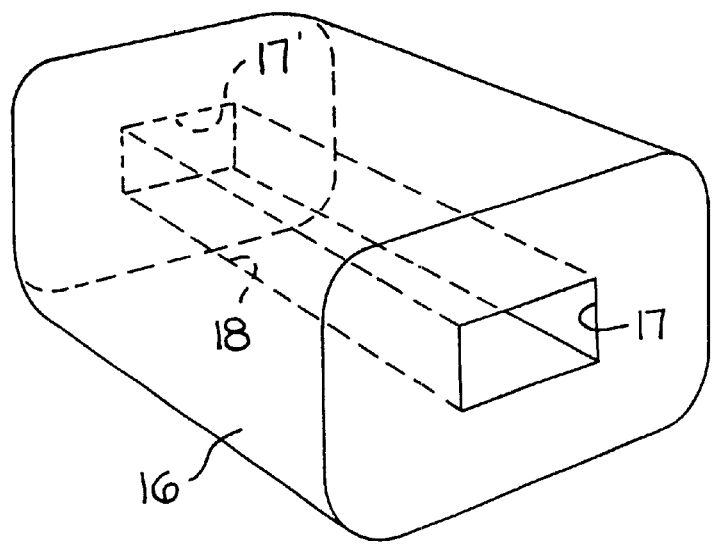

Referring now to FIGS. 2, 3, and 7, the sponge 16, which has a length "sl", a width "sw", and a thickness "st", includes a cavity 18, having at least one open end 17. The trunk 24 of the body 12 fits snuggly in the open end 17, and can be secured, if necessary, to the sponge 16 with glues or adhesives, as is known in the art. In the preferred embodiment, the cavity 18 has at least two open ends 17, 17', and is sufficiently large that a body 12 can be positioned in each end 17, 17' and a reservoir 19 remains. The sponge 16 can be made of natural sponge materials or from any foamed synthetic material that exhibits sponge-like properties. Optionally, the sponge 16 may further include properties that allow the sponge to have a exfoliating or brush-like texture. In addition, if desired by the user, the reservoir 19 can be filled with an antibacterial agent, a disinfectant soap, an antiseptic agent, or another skin cleansing product commonly used in a medical facility, for example Savlon®, Povidine®, parachilorometaxylene (PCmX), chlorhexidinegluconate, or similar chemical products, including products in powdered or gel form, or the sponge 16 can be impregnated with an antibacterial agent or disinfectant soap or other skin cleansing product commonly used in a medical facility.

Referring to FIGS. 1–7, in a preferred embodiment, a scrub device 10 has a sponge 16 made from foamed polyurethane, and has a length "sl" of about 3.5", a width of about 3.0", and a thickness "st" of about 1.75". A cavity 18, having a width of approximately 1.25" and a height of about 0.5", extends through the sponge 16. Two bodies 12 made of polyethylene are fitted into the cavity 18, one body 12 being at either end. The length "l" of each body 12 is about 0.6"; the trunk 24 of each body 12 has a width "x" of about 1.25", and a thickness "z" of about 0.5"; and the head 20 has a width "w" of about 2.0", and a thickness "t" of about 1.0". The bristles 14 are made of polyurethane and are co-extruded with the body 12 in a random pattern. The bristles 14 vary in length from about 0.2" to about 0.4". Powdered antibacterial soap fills the reservoir 19.

Figure 8:
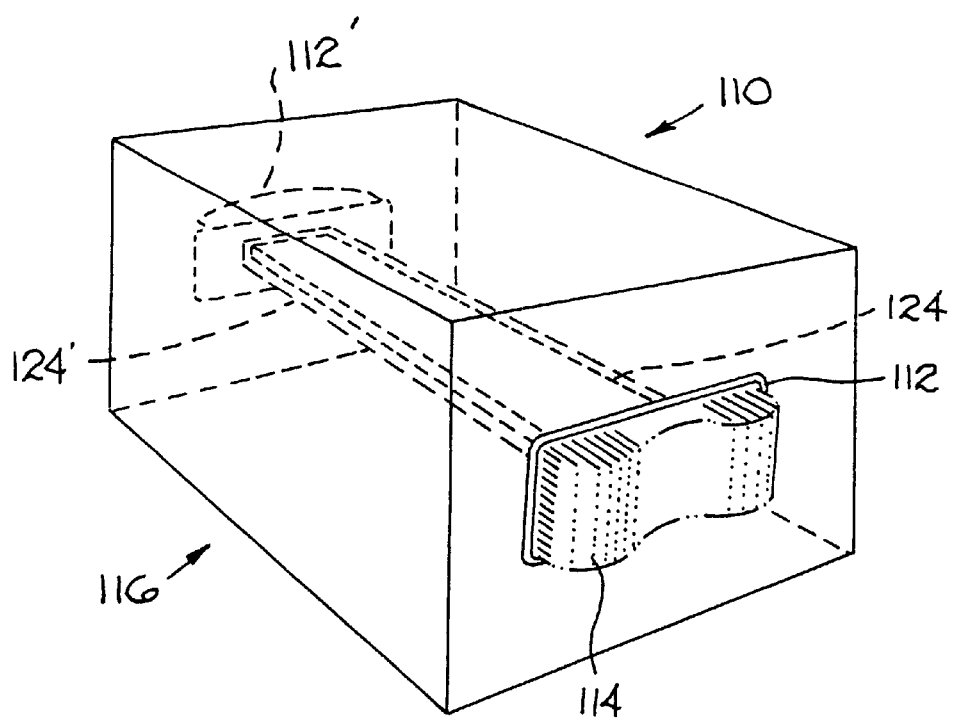
FIG. 8 is a perspective view of a first alternative embodiment of the device of FIG. 1a wherein the first body has a closed trunk and the second body has a sleeve-like trunk.
Figure 9:
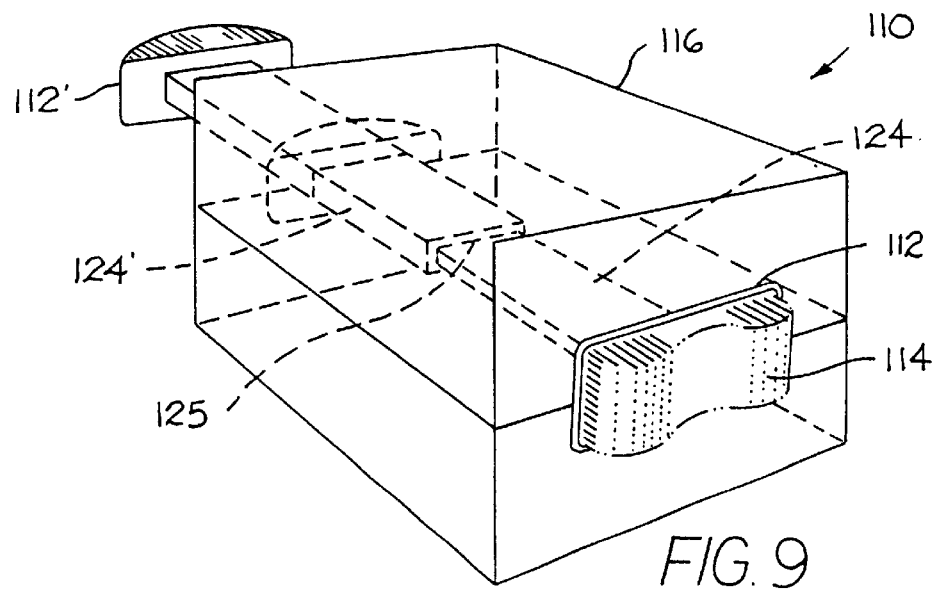
FIG. 9 is an exploded perspective view of the bodies of the device of FIG. 8, with the sponge removed.

An alternative embodiment 110 of the scrub device of FIG. 1 is shown in FIGS. 8 and 9. The scrub device 110 has as major components two bodies 112, 112', bristles 114, 114', and a sponge 116. The first body 112, the bristles 114, 114', and the sponge 116 are essentially identical to the body 12, the bristles 14, and the sponge 16 of device 10, respectively. The second body 112' is similar to the body 12 except that the trunk 124' is hollow forming a sleeve-like structure 125' that can receive the first trunk 124. In the preferred embodiment, the trunk 124 fits sufficiently tightly within the sleeve 125' so that no additional adhesive is required to hold the bodies in the sponge 116.

Referring to FIGS. 8 and 9, in a preferred embodiment, a scrub device 110 has a sponge 116 and bristles 114, 114' that are the same as the sponge 16 and bristles 14 of device 10 of Example 1. The device 110 has two bodies 112, 112' that are made of polyvinyl chloride (PVC), and each has a length "l" of about 3.0". Each body 112, 112' has a head 120, 120' with a width "w" of about 2.0", and a thickness "t" of about 1.0". The trunk 124 of the first body 112 has a width "x" of about 0.5", and a thickness "z" of about 0.25". The trunk 124' of the second body 112' forms a sleeve 125' with an outside width "x" of about 0.6", and an outside thickness "z" of about 0.35". The inside dimensions of the sleeve 125' are sufficiently large to accommodate the trunk 124 of the first body 120.

Figure 10:
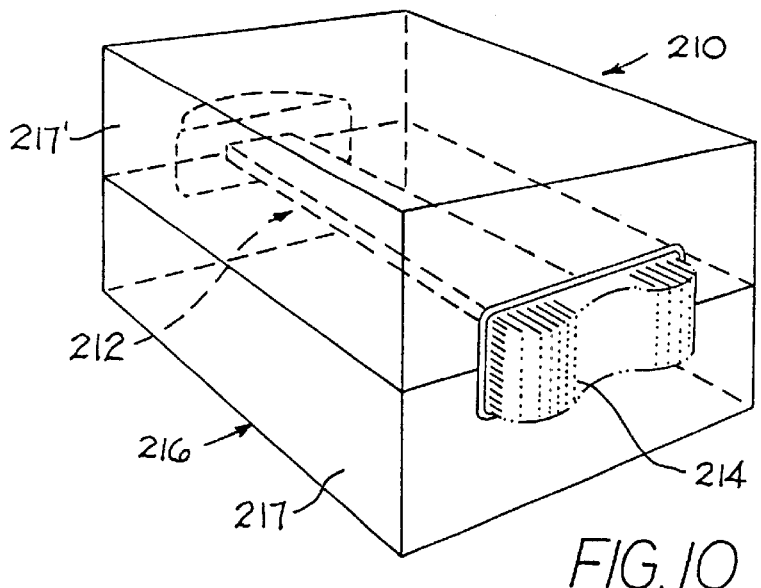
FIG. 10 is a perspective view of a second alternative embodiment of the device of FIG. 1a wherein the body has one trunk attached to two heads.
Figure 11:
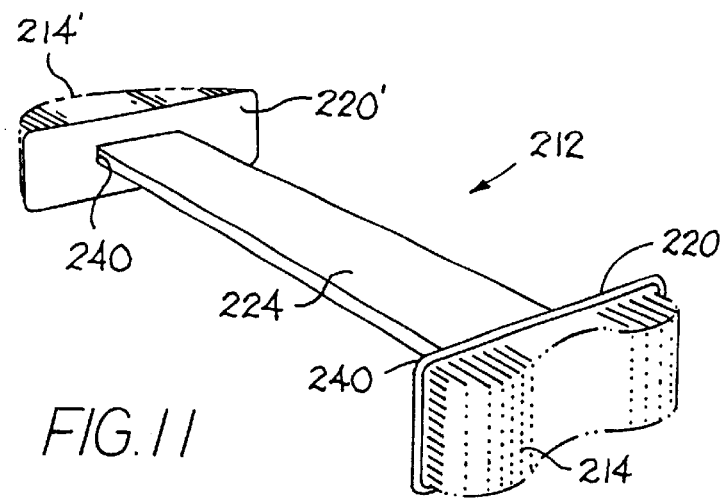
FIG. 11 is a perspective view of the body of the device of FIG. 10 with the sponge removed.

Alternatively, as shown in FIGS. 10 and 11, the scrub device 210 can have a body 212 that has single trunk 224 with two heads 220, 220'. The heads 220, 220' and the bristles 214, 214' are essentially identical to the head 20 and bristles 14, respectively, of device 10. The single trunk 224 is similar to the trunk 24 except that the single trunk 224 has a first head 220 on one end 240 of the trunk 224 and a second head 220' on the second end 240'. Because the two-headed body 212 can be difficult to pass through a channel in the sponge 216, the sponge 216 may be formed around the trunk 224 in the manufacturing process, as is known in the art, leaving the heads 220, 220' exposed. Alternatively, the sponge 216 may be prepared in multiple pieces 217, 217' which are then attached to the two-headed trunk 224 and to each other with glues or adhesives, as is known in the art, or the sponge 216 may include a lengthwise slit (not shown) to allow the two-headed trunk 224 to be positioned within the sponge 216, which can then be held closed with glues or adhesives.

Referring to FIGS. 10 and 11, in a preferred embodiment, a scrub device 210 has bristles 214, 214' that are the same as bristles 14 of device 10 of FIGS. 1–7. The device 210 has a body 212 that includes a trunk 224 connecting two heads 220, 220'. The body 212 is made of amorphous polyethylene terephthalate (APET), and has a length "l" of about 3.2"; each head 220, 220' has a width "w" of about 2.0", and a thickness "t" of about 1.0"; and the trunk 224 has a width "x" of about 0.5", and a thickness "z" of about 0.25". The sponge 216 is formed from two pieces 217, 217' of sea sponge material, each cut into an essentially rectangular shape measuring about 3.0" by about 2.5" by about 0.9". The trunk 224 of the body 212 is sandwiched between the foam pieces 217, 217' such that only the heads 220, 220' and bristles 214, 214' are exposed, and the sponge pieces 217, 217' are glued to the trunk 224 and to each other with a thin layer of epoxy. The sponge 216 is impregnated with parachlorometaxylene.

An alternative embodiment 310 of the scrub device 210 of FIGS. 10–11 is shown in FIGS. 12–17. Similar to the scrub device 210, the scrub device 310 has a body 312, made from any plastic or polymer that can be molded into a semi-rigid part, that has a single trunk 324 and two heads 320, 320' attached to the trunk 324. Preferably, the heads 320, 320' are essentially mirror images of each other, although other configurations can include the inventive features described herein. The trunk 324 bisects each head 320, 320', forming left 326, 326' and right 328, 328' branches. Preferably, the left 326 and right 328 branches of the first head 320 are essentially mirror images of each other, although this is not required. Similarly, in the preferred embodiment, the left 326' and right 328' branches of the second head 320' are essentially mirror images of each other, although this is not required. The branches 326, 326', 328, 328' lie in the same horizontal plane as the trunk 324, and each is displaced from the trunk 324 by a predetermined distance "s". In the preferred embodiment, the device 310 has a slightly rounded shape, and the distance between the trunk 324 and each branch 326, 326', 328, 328' is essentially equal, with "s" defined as a radial distance from the midpoint "c" of the trunk 324 to the inner edge 331, 331' of each head 320, 320'. The body 312 has a length "rl", defined as the distance from the outside edge 330 of the first head 320 at the midline "m" of the trunk 324 to the outside edge 330' of the second head 320' at the midline "m" of the trunk 324; a width "rw" for each branch, defined as the distance from the outermost edge 334, 334' of the left branch 326, 326' to the outermost edge 336, 336' of the right branch 328, 328'; and a thickness "rt", defined as the thickest point of the body 312.

The heads 320, 320', which have each have a midline "mt$_1$", "mt$_2$", further include one or more cavities 338, which have a depth "d", bored into the outside edges 330, 330'. The cavities 338 can have any configuration and dimension that will fit the heads 320, 320', and in the preferred embodiment, the cavities 338 have a cylindrical shape. A space or gap 342 which exposes the outside edge 330, 330' can optionally remain between the individual cavities 338.

The bristles 314 are made from any plastic, polymer or natural fiber that can be formed into semi-rigid strands, such as nylon or straw. The bristles 314, which can vary in length "b" as desired by the user, are mounted in the cavities 338 and protrude from the cavities 338 to form a brush-like structure 346 along the outside edges 330, 330' of the heads 320, 320'. Depending on the configuration of the cavities 338, the bristles 314 may span the heads 320, 320' in a continuous line (not shown), or the bristles 314 may be grouped into clusters 340, as shown in FIGS. 12–17. As is known in the art, the bristles 314 are held within the cavities 338 by glue, adhesive or combinations thereof.

Referring now to FIGS. 12, 13 and 14, the sponge 316, which has a length "rsl", a width "rsw", and a thickness "rst", envelopes the trunk 324 and the heads 320, 320' so as to leave only the outside edges 330, 330' and the bristles 314 exposed. The sponge 316 can be made of natural sponge materials or from any foamed synthetic material that exhibits sponge-like properties. Optionally, the sponge 316 may further include properties that allow the sponge to have a exfoliating or brush-like texture. In addition, if desired by the user, the sponge can be impregnated with an antibacterial agent, a disinfectant soap, an antiseptic agent, or another skin cleansing product commonly used in a medical facility, for example Savlon®, Povidine®, parachlorometaxylene (PCmX), hlorhexidinegluconate, or similar chemical products. The sponge 316 can be secured to the body 312 with glues or adhesives, as is known in the art, or it 316 can be foamed around the body 312 in the manufacturing process, as is also known in the art. For easier handling, the sponge 316 may be sculpted to better fit the contour of the hand and/or fingers.

Referring to FIGS. 12–17, in a preferred embodiment, the body 312 is made of glycol-modified polyethylene terephthalate (PETG); each branch 326, 326', 328, 328' is separated from the midpoint "c" of the trunk 324 by a radius of about 3.5"; the body 312 has a length "rl" of about 2.250", a width "rw" of about 2.250", and a thickness "rt" of about 0.25". A plurality of cavities 338 are bored along the outside edges 330, 330' of the heads 320, 320', with each cavity having a diameter of about 0.1" and a depth of about 0.187". The cavities 338 are essentially evenly spaced with the neighboring centers being separated by from about 0.187" to about 0.25", and the cavities 38 are aligned essentially along the midlines "mt$_1$", "mt$_2$" of the heads 320, 320'. The bristles 314 are made of nylon, vary in length "b", are grouped into clusters to fit snuggly within the cavities 338, and are held within the cavities 338 by hot-melt adhesive. The sponge 316, having a length "rsl" of 3.5", a width "rsw" of 2.75", and a thickness "rst" of 1.5", is made from foamed polyurethane and is impregnated with antibacterial soap.

A primary function of the body 12 of the scrub device 10 is to support the bristles 14 and the sponge 16. As shown in FIGS. 18–27, the body can have alternative forms, such as a shell-like structure 512, 612 or a frame-like structure 712, and still serve the required support function.

Figure 18:
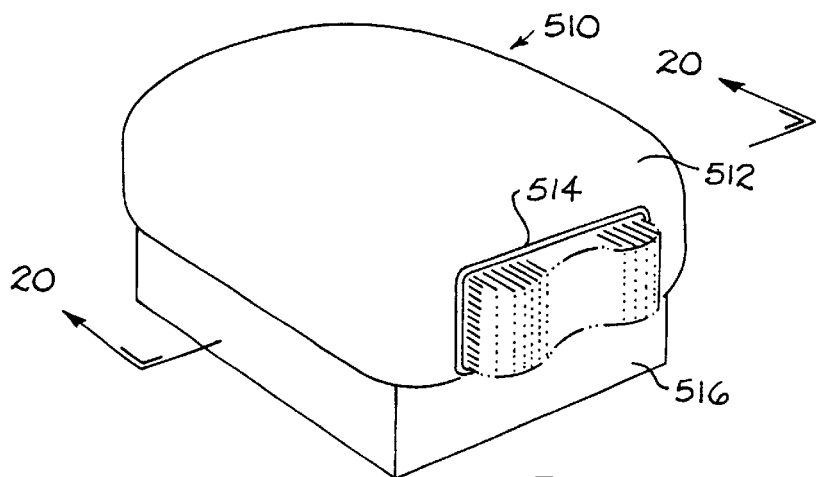
FIG. 18 is a perspective view of a surgical scrub device made in accordance with the present invention wherein the body is a flexible shell, with the bristles projecting from the sides of the shell, and the sponge fitting into the body.
Figure 19:
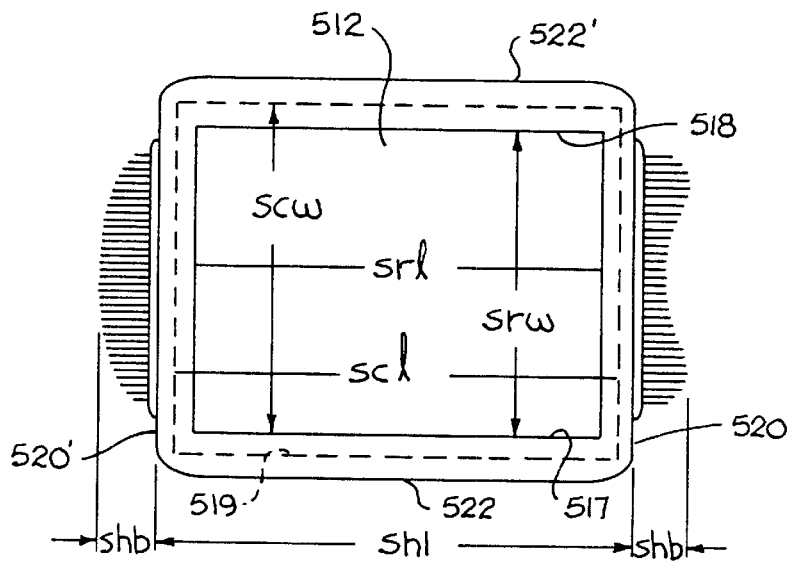
FIG. 19 is a top view of the device of FIG. 18, with the sponge removed.
Figure 20:
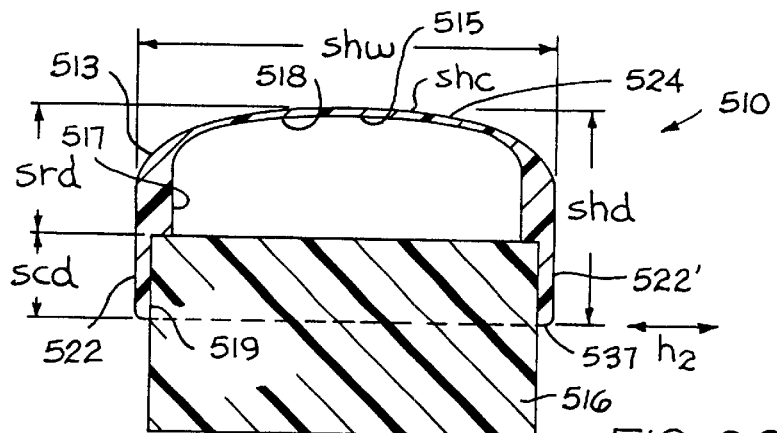
FIG. 20 is a cut-away side view of the device of FIG. 18, with the sponge removed.
Figure 21:
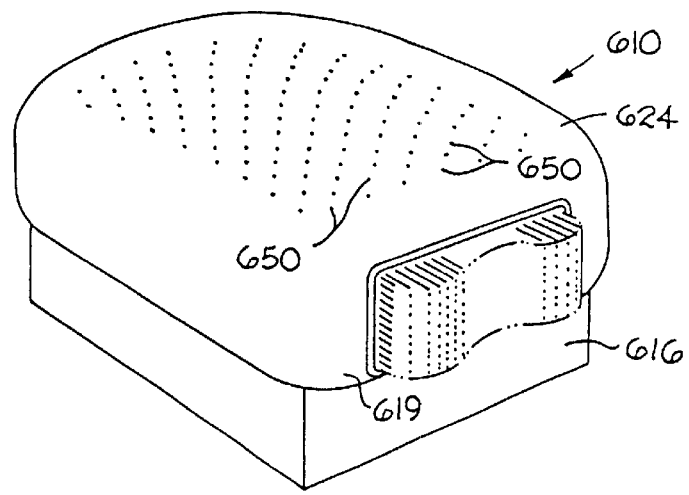
FIG. 21 is a perspective view of an alternative embodiment of the surgical scrub device of FIG. 18 but including apertures on the cover of the shell.

Referring specifically to FIGS. 18–20, a scrub device 510 constructed in accordance with the present invention has as major components at least one semi-rigid body 512, bristles 514, and a sponge 516. The body 512 has a shell-like structure with the bristles 14 projecting from the shell 512 and the sponge 516 fitting within the shell 512.

Referring again to FIGS. 19 and 20, the shell-like body 512 is made from any plastic or polymer that can be molded into a semi-rigid part, such as polyethylene, polypropylene, polystyrene, thermoplastic polyester, polycarbonate, polyurethane, high density linear polyethylene, polyvinyl chloride (PVC), polyethylene terephthalate (PET), amorphous polyethylene terephthalate (APET), high density polyethylene/ethylvinyl acetate (HDPE/EVA) copolymer, glycol-modified polyethylene terephthalate (PETG), acrylonitrile butadiene styrene (ABS). cellulose acetate, or combinations thereof. In the preferred embodiment, the plastic shell 512 will also exhibit elastic properties, i.e. the user can apply pressure to the shell 512 to contract the shell 512 slightly and, when the pressure is released, the shell 512 returns to its original shape. A variety of monomer and plasticizer combinations may be used to provide these properties to the shell 512, as is known in the art.

The shell 512, which has an exterior face 513 and an interior face 515, defines a top 524 and sides 520, 520', 522, 522', which extend from the top 524 and define a frame 519. The bristles 514 can protrude from the exterior face 513 of the top 524, or from at least one side of the frame 519, or from a combination thereof. In the preferred embodiment, the bristles 514 protrude from two sides 520, 520'. The interior face 515 defines a cavity 518. The cavity 518 may be tiered, as shown in FIGS. 19–20, if desired by the user, to create an upper reservoir 517 separate from the frame 519, although having tiers is not necessary. An advantage of the tiered cavity 518 is that a cleansing agent or an antibacterial agent or a disinfectant soap or other skin cleansing product commonly used in a medical facility, including products in powdered or gel form, can be stored in the reservoir 517 and the sponge 516 fitted in the frame 519. The shell 512 has a length "shl", defined as the distance from a first side 520 to an opposing second side 520'; a width "shw", defined as the distance from a third side 522 to an opposing fourth side 522'; a shell depth "shd", defined as the distance from the crown of the top "shc" to the lower edge 537 of the frame 519; a cavity end width "scw"; a cavity end length "sel"; a cavity end depth "scd"; a cavity reservoir width "srw"; a cavity reservoir length "srl"; and a cavity reservoir depth "srd". The lower edge 537 of the frame 519 defines a horizontal plane "$h_2$".

The bristles 514 are made from any plastic or polymer that can be co-extruded with the shell 512, and are preferably co-extruded so as to protrude a distance "shb" from the first and second sides 520, 520', forming a brush-like structure 46. Depending on the application, the bristles 514 may span the sides 520, 520' in a single continuous row (not shown), in a series of rows (FIGS. 19–20), or in a random pattern (not shown). The distance "shb" may be essentially equal for each bristle (not shown), or may vary, such as shown in FIG. 19. As shown in FIG. 18, the bristles 514 lie in horizontal planes that are essentially parallel to the plane "$h_2$".

Referring now to FIG. 18, the sponge 16, which has a length "spl", a width "spw", and a thickness "spt", fits snuggly in the frame 519 of the cavity 518, and can be secured, if necessary, to the cavity 518 with glues or adhesives, as is known in the art. The sponge 16 can be made of natural sponge materials or from any foamed synthetic material that exhibits sponge-like properties. Optionally, the sponge 516 may further include properties that allow the sponge to have a exfoliating or brush-like texture. In addition, if desired by the user, the reservoir 517 can be filled with an antibacterial agent, a disinfectant soap an antiseptic agent, or another skin cleansing product commonly used in a medical facility.

Referring to FIGS. 18–20, in a preferred embodiment, a scrub device 510 has a shell 512 made of polypropylene. The shell 512 has a length "shl" of about 3.5"; a width "shw" of about 3.0"; a shell depth "shd" of about 1.0"; a cavity end width "cw" of about 2.875"; a cavity end length "cl" of about 3.25"; a cavity end depth "cd" of about 0.5"; a cavity reservoir width "rw" of about 2.5"; a cavity reservoir length "rl" of about 3.0"; and a cavity reservoir depth "rd" of about 0.4". The bristles 514 are made of polypropylene and are co-extruded with the shell 512 in a random pattern. The bristles 514 vary in length from about 0.2" to about 0.5". A sponge 516 made from foamed polyurethane, has a length "spl" of about 3.25", a width of about 2.875", and a thickness "st" of about 0.75". The sponge 516 is fitted snuggly into the receiving end 519 of the shell 512 and is held in position without glue or adhesives. Powdered antibacterial soap fills the reservoir 519.

Figure 22:
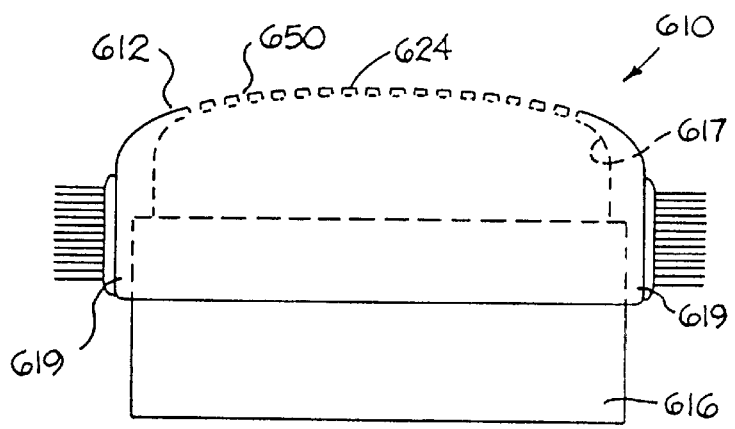
FIG. 22 is a side view of the device of FIG. 21.
Figure 23:
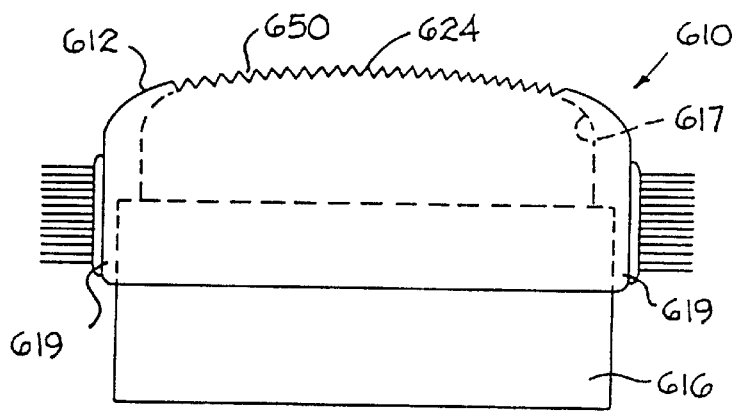
FIG. 23 is a side view of the device of FIG. 21 showing an alternative pore structure in the closed position.

An alternative embodiment 610 of the scrub device of FIG. 18 is shown in FIGS. 21–24. The scrub device 610 is essentially identical to the device 510 except that a plurality of pores 650 are provided along the top 624 of the shell 612, and if desired, along the frame 619. The pores 650 may be short channels that allow moisture to pass into the reservoir 617 at all times, as shown in FIG. 22, or the pores 650 can be designed to be pressure sensitive, as shown in FIGS. 23 and 24. If the pores 650 are pressure sensitive, when no pressure is applied to the shell 612 (FIG. 23), the pores 650 are closed, thereby preventing moisture or other contaminants from entering the reservoir 617. However, when pressure is exerted on the shell 612 (FIG. 24), the pores 650 open to allow moisture to enter the reservoir 617 and to allow the cleansing agent in the reservoir 617 to exit.

Figure 25:
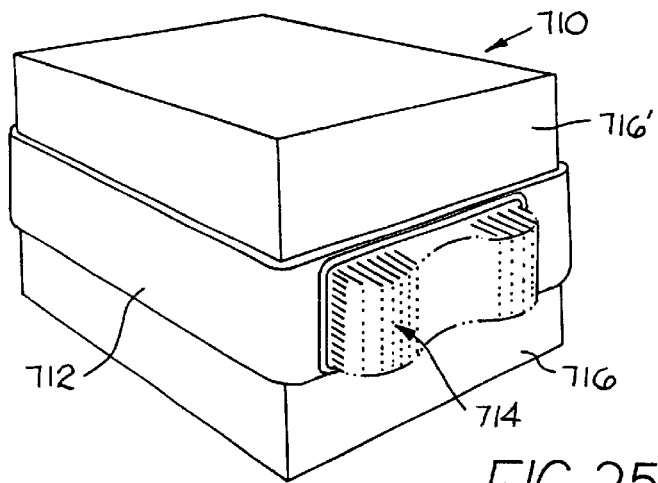
FIG. 25 is a perspective view of a second alternative embodiment of the device of FIG. 18 wherein the top is removed to form a frame.
Figure 26:
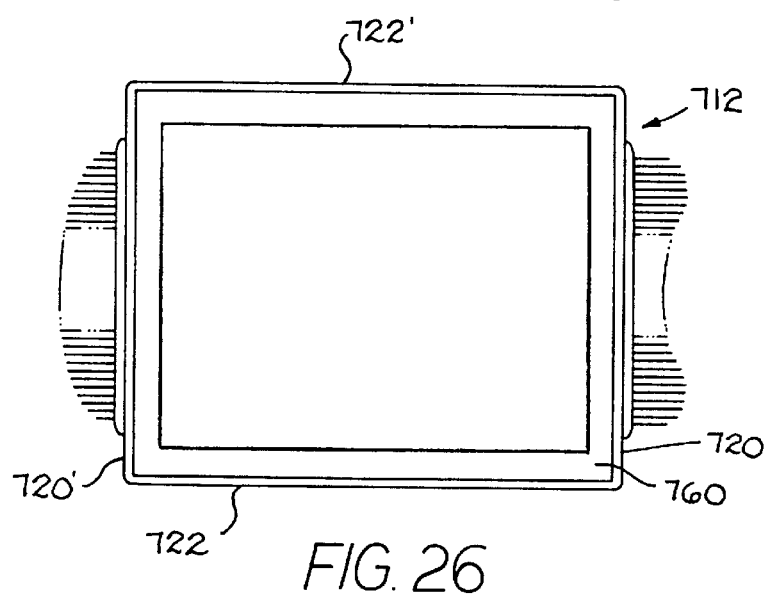
FIG. 26 is a top view of the device of FIG. 25, with the sponges removed.
Figure 27:
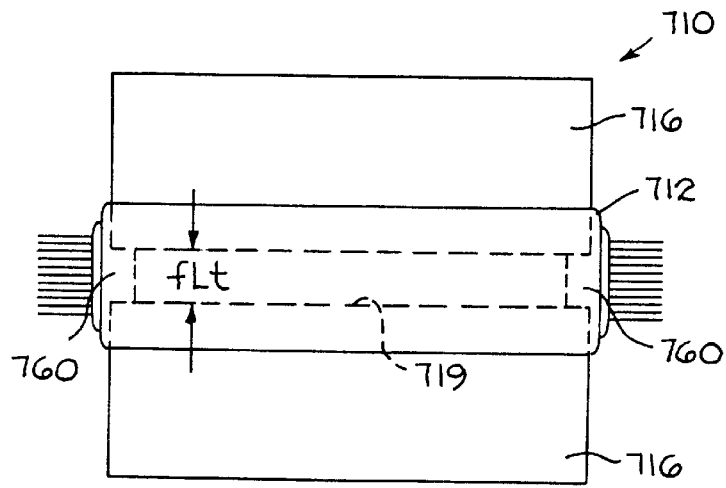
FIG. 27 is a side view of the device of FIG. 25.

As shown in FIGS. 25–27, a scrub device 710 that is similar to device 510 can be made by removing the top 524 from the shell 512 and leaving a frame-like structure 712. The frame 712, having sides 720, 720', 722, 722', and having a length "fl", a width "fw", and a thickness "ft", is made from any plastic or polymer that can be molded into a semi-rigid part. The frame 712 includes a ledge 760, having a width "flw" and a thickness "flt", along the interior surface. Sponges 716, 716' are mounted in the frame 712, and are separated from each other by the ledge 760, creating a reservoir 719 between the sponges 716, 716' that can hold a cleansing agent. The bristles 714 project from at least one side of the frame 712.

Referring to FIGS. 25–27, in a preferred embodiment, a scrub device 710 has a frame 712 made of polyethylene. The frame 712 has a length "fl" of about 3.75"; a width "fw" of about 3.25"; and a thickness "ft" of about 1.0". A continuous ledge 760, having a width "flw" of about 0.25" and a thickness "flt" of about 0.25", is along the interior surface. Bristles 714 made of polyethylene and co-extruded with the frame 712 in a random pattern project from two sides 720, 720' of the frame 712. The bristles 714 vary in length from about 0.2" to about 0.5". Two sponges 716, 716' made from foamed polyurethane, and each having dimensions of about 3.75" by about 3.25" by about 0.75" are fitted snuggly in the frame 712 and are held in position without glue or adhesives. Powdered antibacterial soap fills the reservoir 719.

Although most of the alternative embodiments to the basic surgical scrub device 10 of FIG. 1 presented herein have addressed modifications to the body 12, it is understood that the bristles 14 may be of any materials and formed in any means that a brush-like structure is formed. Further, it is understood that different types of scrubbing or cleaning surfaces can be used to replace all or part of the sponge 16. For example, as shown in the scrub device 810 of FIGS. 28 and 29, the sponge 316 of scrub device 310 shown in FIGS. 12–17 may be replaced by a nylon net scrub unit 850 on one side and by a copper net scrub 852 unit on the opposite side to make a household-type scrubber.

It is understood that, in light of a reading of the foregoing description and drawings, those with ordinary skill in the art will be able to make changes and modifications to the present invention without departing from the spirit or scope of the invention, as defined herein.

What is claimed is:

1. A surgical scrub device comprising:
   at least one semi-rigid body, having a head and a trunk, and said body being made from an extrudable polymeric material, and said trunk defining a horizontal plane;
   a first set of bristles projecting from said head and being essentially parallel to the horizontal plane, said bristles being made from an extrudable polymeric material and being co-extruded with said body;
   a sponge at least partially circumscribing and attached to said trunk for cleaning skin portions of a surgical team member whereby said sponge may be manually gripped to scour the nails of said team member with said first set of bristles.

2. The surgical scrub device of claim 1 wherein the polymeric material is selected from the group consisting of polyethylene, polypropylene, polystyrene, thermoplastic polyester, polycarbonate, polyurethane, high density linear polyethylene, polyvinyl chloride (PVC), polyethylene terephthalate (PET), amorphous polyethylene terephthalate (APET), high density polyethylene/ethylvinyl acetate (HDPE/EVA) copolymer, glycol-modified polyethylene terephthalate (PETG), acrylonitrile butadiene styrene (ABS), cellulose acetate, or combinations thereof.

3. The surgical scrub device of claim 1 wherein the polymeric material further includes a plasticizer.

4. The surgical scrub device of claim 1 wherein said body further includes a tail extending from the trunk.

5. The surgical scrub device of claim 4 wherein the tail further includes a second set of bristles projecting along the horizontal plane from the tail.

6. The surgical scrub device of claim 1 further including a second body, having a head and a trunk, and defining a horizontal plane, and a second set of bristles projecting along the horizontal plane from the head, wherein said sponge is also reversibly attached to the trunk of the second body.

7. The surgical scrub device of claim 1 wherein said bristles of the first set of bristles are of essentially the same length.

8. The surgical scrub device of claim 1 wherein said bristles of the first set of bristles are of different lengths.

9. The surgical scrub device of claim 1 wherein said sponge envelopes the trunk.

10. The surgical scrub device of claim 1 wherein said sponge is impregnated with a cleansing agent.

11. A surgical scrub device comprising:
a semi-rigid frame having a ledge which projects inwardly toward a center of the frame along a horizontal plane, said ledge defining an upper portion and a lower portion within said frame and said frame being made from an extrudable polymeric material;
at least one set of bristles projecting outwardly from the frame of said body and being essentially parallel to the horizontal plane, said bristles being made from an extrudable polymeric material and being co-extruded with said body;
a first sponge secured within the upper portion of said frame and abutting said ledge; and
a second sponge secured within the lower portion of said frame and abutting said ledge.

12. The surgical scrub device of claim 11 wherein the polymeric material is selected from the group consisting of polyethylene, polypropylene, polystyrene, thermoplastic polyester, polycarbonate, polyurethane, high density linear polyethylene, polyvinyl chloride (PVC), polyethylene terephthalate (PET), amorphous polyethylene terephthalate (APET), high density polyethylene/ethylvinyl acetate (HDPE/EVA) copolymer, glycol-modified polyethylene terephthalate (PETG), acrylonitrile butadiene styrene (ABS), cellulose acetate, or combinations thereof.

13. The surgical scrub device of claim 11 wherein the polymeric material further includes a plasticizer.

14. The surgical scrub device of claim 11 wherein said bristles of the first set of bristles are of essentially the same length.

15. The surgical scrub device of claim 11 wherein said bristles of the first set of bristles are of different lengths.

16. The surgical scrub device of claim 11 wherein said sponge is impregnated with a cleansing agent.

17. The surgical scrub device of claim 11 wherein a reservoir is formed between said first sponge and said second sponge.

18. The surgical scrub device of claim 17 wherein said reservoir contains a cleaning agent.

19. A surgical scrub device comprising:
at least one semi-rigid body, having a head and a trunk, and defining a horizontal plane, and said head having at least two branches wherein the branches lie in the horizontal plane;
a first set of bristles projecting from the branches of said head and away from said trunk, and said bristles lying in the horizontal plane;
a sponge at least partially circumscribing and attached to said trunk for cleaning skin portions of a surgical team member whereby said sponge may be manually gripped to scour the nails of said team member with said first set of bristles.

20. The surgical scrub device of claim 19 wherein said body is made from a polymeric material.

21. The surgical scrub device of claim 20 wherein the polymeric material further includes a plasticizer.

22. The surgical scrub device of claim 19 wherein said body further includes a tail extending from the trunk, and said tail further includes a second set of bristles projecting away from said trunk and lying in the horizontal plane.

23. The surgical scrub device of claim 19 wherein said bristles are made from a polymeric material.

24. The surgical scrub device of claim 19 wherein said bristles are made from a natural fiber, and wherein the head of said body further includes cavities, and the bristles are secured to said head within the cavities.

25. The surgical scrub device of claim 19 wherein said sponge is impregnated with a cleansing agent.

26. A surgical scrub device comprising:
a semi-rigid body, being made from an extrudable polymeric material, said body having a top with a shell-like structure, the shell having a interior surface and an exterior surface, and the shell further defining a cavity on the interior surface, and said body having a base defining a horizontal plane;
at least one set of bristles projecting from the base of said body and being essentially parallel to the horizontal plane, said bristles being made from an extrudable polymeric material and being co-extruded with said body; and
a sponge secured within the base of said body for cleaning skin portions of a surgical team member.

27. The surgical scrub device of claim 26 wherein said shell-like top further includes a plurality of pores on the top.

28. The surgical scrub device of claim 27 wherein the pores are open channels allowing unimpeded transport of materials from the exterior surface to the interior surface.

29. The surgical scrub device of claim 27 wherein the pores have a closed first position and an opened second position, and where the pores move from a first to a second position by the application of pressure.

* * * * *